United States Patent
Nemori et al.

(10) Patent No.: US 6,790,609 B1
(45) Date of Patent: Sep. 14, 2004

(54) THIN MEMBRANE FOR DETECTING THIOL-CONTAINING COMPOUNDS

(75) Inventors: Ryoichi Nemori, Minami-ashigara (JP); Junji Nishigaki, Minami-ashigara (JP); Yutaka Tamura, Minami-ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/786,883

(22) PCT Filed: Sep. 10, 1999

(86) PCT No.: PCT/JP99/04933

§ 371 (c)(1),
(2), (4) Date: Jun. 7, 2001

(87) PCT Pub. No.: WO00/16094

PCT Pub. Date: Mar. 23, 2000

(30) Foreign Application Priority Data

Oct. 9, 1998 (JP) .......................... 10/256839

(51) Int. Cl.$^7$ ............................... C12Q 1/00
(52) U.S. Cl. ............................ 435/4; 435/181
(58) Field of Search ............... 435/4, 40.5, 181

(56) References Cited

U.S. PATENT DOCUMENTS

| 4,021,198 | A | * | 5/1977 | Fujita et al. | |
| 5,958,430 | A | * | 9/1999 | Campbell et al. | 424/400 |
| 6,203,706 | B1 | * | 3/2001 | Schwind et al. | 210/645 |
| 2003/0148399 | A1 | * | 8/2003 | Nemori et al. | 435/7.4 |

FOREIGN PATENT DOCUMENTS

| EP | 0 546 939 A1 | 6/1993 |
| GB | 2200989 A | * 8/1988 |
| JP | 5-130897 | * 5/1993 |
| JP | 6-16619 | * 1/1994 |

OTHER PUBLICATIONS

WO 97/05482. Kerschensteiner (1997). A colorimetric method of detecting thiol or mercaptan compounds and its use for oral malodor determination.*

Derwent abstract (Acc no 1993–349181) of SU 0769124. Teroganesyan (1992). Determination of mercaptan content in petroleum fuels—by passing sample through layer of zeolite modified with silver ions and measuring the height of formed colored zone.*

Patent Abstracts of Japan, 3–021331, vol. 015, No. 141, Jan. 30, 1991.

Patent Abstracts of Japan, 7–097767, vol. 1995, No. 7, Apr. 11, 1995.

Patent Abstracts of Japan. 6–016619, vol. 018, No. 222, Jan. 25, 1994.

* cited by examiner

Primary Examiner—Ralph Gitomer
(74) Attorney, Agent, or Firm—Sughrue Mion, PLLC

(57) ABSTRACT

A method for measuring a thiol group-containing compound, which comprises the steps of (1) contacting a sample containing a thiol group-containing compound with a thin membrane comprising a microparticle of a substance selected from the group consisting of a metal and a metal compound and comprising a hydrophilic binder; and (2) detecting a color change on the thin membrane resulting from interaction of the thiol group-containing compound and the microparticle, and a thin membrane used for said method. A thiol group containing compound such as an alkylmercaptan or a protein containing thiol groups can be conveniently and accurately measured.

4 Claims, No Drawings

THIN MEMBRANE FOR DETECTING THIOL-CONTAINING COMPOUNDS

This application is the National Stage of International Application No. PCT/JP99/04933, filed Sep. 10, 1999, which claims the benefit of Application Japan 10/256839 filed Oct. 9, 1998.

FIELD OF THE INVENTION

The present invention relates to a convenient method for measuring a thiol group-containing compound and a thin membrane used for said method.

BACKGROUND ART

Thiol group-containing compounds have various functions attributable to reactivity of thiol groups. Accordingly, they are utilized in chemical industries, and they also play important roles in a living body such as glutathione, coenzyme A and so forth. For detection and quantitative assay of trace amounts of thiol group-containing compounds, methods having been applied so far include methods of direct measurement using separation and analysis means such as gas chromatography and liquid chromatography, or methods comprising the steps of reaction with a compound reactive to a thiol group such as maleimide derivatives, and then modification with a readily detectable compound such as a fluorescent dye and detection of the resulting compound. However, these methods have problems in that they require large-scale apparatuses or need skills for operation. Therefore, it has been desired to develop a method for easily and accurately measuring thiol group-containing compounds contained is biosamples in chemical laboratories, test facilities, clinical situations and so forth.

DISCLOSURE OF THE INVENTION

An object of the present invention is to provide a method for conveniently and accurately measuring a thiol group-containing compound. More specifically, the object of the present invention is to provide a method for conveniently and accurately measuring a thiol group-containing compound, for example, alkylmercaptans, arylmercaptans, amino acid derivatives such as cysteine and glutathione, proteins containing free thiol groups and so forth. Another object of the present invention is to provide a method for measuring a thiol group-containing compound which has the aforementioned characteristic features and is capable of accurately determining intratissular localization of said compounds which are derived from cancer cells localized in test tissues. A further object of the present invention is to provide a thin membrane used for the aforementioned method for measurement of a thiol group-containing compound.

The inventors of the present invention conducted researches to achieve the foregoing objects, and as a result, they found that, when a solution or a living tissue slice which contains a thiol group-containing compound was closely contacted with a thin membrane comprising micropaiticles of a substance selected from the group consisting of a metal and a metal compound together with a hydrophilic binder, the thiol group-containing compound contained in the solution or the living biological tissue slice interacted with the substance selected from the group consisting of a metal and a metal compound to cause color change such as change of color tone and coloration, and that the thiol group-containing compound contained in the sample was conveniently and accurately measurable by detecting the color change through visual observation, under optical microscope, or by spectroscopic means or the like. The inventors also found that detection ability of the aforementioned thin membrane was further improved by adding a crosslinking agent to the aforementioned thin membrane. The present invention was achieved on the basis of these findings.

The present invention thus provides a method for measuring a thiol group-containing compound, which comprises the steps of: (1) contacting a sample containing a thiol group-containing compound with a thin membrane comprising a microparticle of a substance selected from the group consisting of a metal and a metal compound and comprising a hydrophilic binder, and (2) detecting a color change on the thin membrane resulting from interaction of the thiol group-containing compound and the microparticle.

The following methods are examples of preferred embodiments of the aforementioned method of the present invention.

1 A method for measuring a thiol group-containing compound which comprises the steps of:
(1) dropping a solution containing a thiol group-containing compound onto a thin membrane comprising a microparticle of a substance selected from the group consisting of a metal and a metal compound and comprising a hydrophilic binder,
(2) optionally drying the dropped solution, and then subjecting the thiol group-containing compound in the solution to interact with the microparticle, and
(3) detecting a color change on the thin membrane resulting from the interaction of the thiol group-containing compound and the microparticle.

In the aforementioned embodiment, the step (2) is usually performed by leaving the thin membrane under saturated humidity at a temperature of from room temperature to 70° C. for several minutes to several hours.

2 A method for measuring a thiol group-containing compound which comprises the steps of:
(1) contacting a frozen slice of a biosample with a thin membrane comprising a microparticle of a substance selected from the group consisting of a metal and a metal compound and comprising a hydrophilic binder and a crosslinking agent,
(2) subjecting the thiol group-containing compound in the biosample to interact with the microparticle, and
(3) detecting a color change on the thin membrane resulting from the interaction of the thiol group-containing compound and the microparticle.

In the aforementioned embodiment, the step (2) is usually performed by leaving the thin membrane, on which the slice is placed, under saturated humidity at a temperature of from room temperature to 70° C. for several minutes to several hours.

3 A method for measuring a thiol group-containing compound which comprises the steps of:
(1) subjecting a solution containing a thiol group-containing compound to be absorbed into an absorptive medium,
(2) contacting the medium containing the absorbed solution with a thin membrane comprising a microparticle of a substance selected from the group consisting of a metal and a metal compound and comprising a hydrophilic binder,
(3) subjecting the thiol group-containing compound in the solution to interact with the microparticle, and
(4) detecting a color change on the thin membrane resulting from the interaction of the thiol group-containing compound and the microparticle.

In the aforementioned embodiment, the absorptive medium used in the step (1) may be, for example, paper, microfilter, gelatin film or the like, and the step (3) is usually performed by leaving the thin membrane under saturated humidity at a temperature of from room temperature to 70° C. for several minutes to several hours.

As a preferred embodiment of the aforementioned method of the present invention, there is provided the aforementioned method wherein the thiol group-containing compound is selected from the group consisting of alkylthiols, arylthiols, amino acids and derivatives thereof, peptide compounds, and proteins. As a preferred embodiment of the aforementioned method of the present invention, there is provided the aforementioned method wherein the biosample is a sample isolated or collected from a mammal including human, more preferably, blood, blood plasma, blood serum, cancer tissue slice, gingival crevice exudate, destructive morbid tissue slice, or destructive morbid tissue extract (for example, rheumatic morbid tissue extract, alveolus blennorrhoea tissue extract and the like). There are also provided the aforementioned method wherein the metal or a metal that constitutes the metal compound is selected from the group consisting of metals of the 2nd period, 3rd period, 4th period, 5th period, and 6th period of the periodic table of elements; and the aforementioned method wherein the metal or a metal that constitutes the metal compound is selected from the group consisting of metals of Group VIb, Group VIIb, Group VIII, Group Ib, Group IIb, Group VIa and Group VIIa in the periodic table of elements.

According to another aspect of the present invention, there is provided a thin membrane used for measurement of a thiol group-containing compound, which contains microparticles of a substance selected from the group consisting of a metal and a metal compound, and hydrophilic colloids. According to a preferred embodiment of the thin membrane of the present invention, the aforementioned thin membrane which further contains a crosslinking agent is provided. This thin membrane is characterized by development of color change resulting from interaction of the thiol group-containing compound and the substance selected from the group consisting of a metal and a metal compound. As preferred embodiments thereof, there are provided the thin membranes for measurement of a thiol group-containing compound which are defined in the aforementioned methods ① through ③. According to further preferred embodiments of said thin membranes, there are provided the aforementioned thin membranes wherein the thin membranes are formed on a flat surface of a support such as object glass and polyethylen terephthalate film; and the thin membranes wherein an undercoat layer is provided between the thin membrane and the support.

BEST MODE FOR CARRYING OUT THE INVENTION

The methods for measuring a thiol group-containing compound according to the aforementioned embodiments basically comprise a step of contacting a sample containing a thiol group-containing compound as an object of the measurement with a thin membrane comprising microparticles of a substance selected from the group consisting of a metal and a metal compound together with a hydrophilic binder (first step), and a step of detecting change of a surface of the thin membrane resulting from interaction of the thiol group-containing compound and the microparticles of a substance selected from the group consisting of a metal and a metal compound (second step). The methods of the present invention have characteristic features in that they enable convenient measurement utilizing a biosample such as a tissue slice and an exudate, and that they achieve high detection accuracy and enable highly sensitive measurement of thiol group-containing compounds even under an optical microscope or by means of an ordinary spectroscopic apparatus. Types of the thiol group-containing compound are not particularly limited, and any compounds having one or more thiol groups may be measured. Examples of the thiol group-containing compound include, but not limited thereto, alkylthiols (for example, methylmercaptan, ethylmercaptan and the like) arylthiols (for example, thiophenol, thionaphthalene, benzylmercaptan and the like), amino acids or derivatives thereof (for example, Cysteine, glutathione and the like), peptide compounds (for example, cysteine residue-containing dipeptide compounds, tripeptide compounds, tetrapeptide compounds, oligopeptide compounds containing five or more amino acid residues and the like), proteins (for example, globular proteins in which cysteine residues are exposed on their surfaces and the like) and so forth.

The term "measurement" used herein should be most broadly interpreted so as to encompass any measurement which can provide any information concerning existence f a thiol group-containing compound, including qualitative and quantitative measurements. When the measurement is performed according to the method of the present invention, if a thiol group-containing compound is contained in a sample, the compound interacts with the micr particles of a substance selected from the group consisting of a metal and a metal compound contained in the thin membrane, and as a result, a detectable color change arises on the thin membrane. The term "interaction" used herein includes various physicochemical and/or chemical interactions which occur between a thiol group-containing compound and a colloid comprising a substance selected from the group consisting of a metal and a metal compound, and the term should be most broadly construed so as to include, for example, formation of a complex or a salt, adsorption, chemical bonding and the like. Moreover, the term also encompasses interaction between a substance produced by an enzymatic action, e.g., a substrate after decomposition by the action of a protease, and a substance selected form a metal and a metal compound.

The color change caused on the thin membrane may be of any type of change. For example, the change may be coloring, deceleration, color tone change or the like. The change may also be spectral change observable in an ultraviolet range or a near infrared ray range. The color change may be a sole change or a combination of two or more changes. The change may be a color change detectable with any one of various measurement techniques available to those skilled in the art, for example, absorbance measurement of a reflected or transmitted ultraviolet ray or visible ray, microscopic or visual observation thereof and so forth, or detectable with any combination of two or more of these measurement techniques.

As for the substance selected from a metal and a metal compound, the metal compound may be either an inorganic metal compound or an organometallic compound. Examples of the metal compound include, for example, oxides, chlorides, bromides, complexes having an organic compound as a ligand and so forth For example, the metal or a metal that constitutes the metal compound may preferably be selected from the group consisting of the 2nd period, 3rd period, 4th period, 5th period, and 6th period of the periodic table of elements of the long period type, and/or those of Group VIb, Group VIIb, Group VIII, Group Ib, Group IIb, Group VIa and Group VIIa in the periodic table of elements. Among them, metals bel nging to the 4th period, 5th period, or 6the period, and Group VIII or Group Ib are more preferred, and gold, silver, copper, platinum, and palladium are most preferred. Among these metals, gold, silver and platinum are particularly preferred, and silver is most preferred. Microparticles composed of two or more kinds of metals and/or metal compounds may also be used. When two or mor kinds of substances are used, they may be used as a mixture. Alternatively, they may be used as an alloy.

More specifically, the substance selected from the group consisting of a metal and a metal compound may be one or more kinds of substances selected from osmium, osmium oxide; silver (mean particle size: 0.01 µm, 0.03 µm, 0.05 µm), silver oxide, silver chloride, silver bromide, silver iodide, silver acetate, silver alginate, silver behenate; gold, gold chloride; cobalt, cobalt oxide, cobalt chloride; Iron, iron oxide, iron chloride; platinum, platinum oxide, platinum chloride; palladium, palladium oxide, palladium chloride; ruthenium, ruthenium oxide, ruthenium chloride; rhodium, rhodium oxide, and rhodium chloride.

Existing states of the microparticles of the substance selected from the group consisting of a metal and a metal compound are not particularly limited so far that the substances are present in the thin membrane. It is preferred that they are uniformly dispersed in the form of a substantially globular microparticle. Particle size of the microparticles is not also particularly limited. For example, mean particle diameter may be from 0.001 µm to 1 µm, more preferably 0.1 µm or less, and most preferably 0.03 µm or less.

As the hydrophilic binder, any materials can be used so long as they are dissolvable in water or can swell by absorption of water. Examples of the hydrophilic binder include, but not limited thereto, naturally occurring polymers, for example, proteins and materials derived from proteins such as gelatin, collagen, casein, transferrin, carboxymethyltransferri, fibronectin, laminbi and elastin; polysaccharides and materials derived from polysacehalides such as cellulose, acetylcellulose, carboymethylcellulose, starch, agarose, carrageenan, dextran, dextrin, chitin, chitosan, pectin and mannan; synthetic polymers such as Poval, polyacrylamide, polyacrylic acid, polyvinylpyrrolidone, polyethylene glycol, polystyrenesulfonic acid and polyarylamine, copolymers comprising monomers of those polymers, gels produced from thos polymers and so forth.

The crosslinking agent used for the production of the this membrane of the present invention may be selected from, for example, those having an action of promoting setting of the thin membrane and/or preventing the swell of the thin membrane after being produced. The kinds of the crosslinking agents are not particularly limited so long as they do not substantially affect the interaction between the thiol group-containing compound and the substance selected from the group consisting of a metal and a metal compound. Inorganic or organic crosslinking agents may be used. For example, crosslinking agents such as chromium salts (chromium alum, chromium acetate and the like); calcium salts (calcium hydroxide, calcium chloride and the like); aluminum salt (aluminum hydroxide, aluminum chloride and the like); aldehydes (formaldehyde, glyoxal, gutaraldehyde and the like); N-methylol compounds (dimethylourea, methyloldimethylhydantoln and the like); dioxane derivatives (2,3-dibydroxydioxane and the like), compounds functioning by activating carboxyl group (calbenium 2-naphtbalenesulfonato-1,1-bispyrrolidino-1-chloro, pyridinium 1-morpholinocarbonyl-3-(sulfonstoaminomethyl) and the like); active vinyl compounds (1,3-bisvinylsulfonyl-2-propanol, 1,2-bis(vinylsulfonylacetamido)ethane, bis (vinylsulfonylmethyl) ether, vinyl polymers having vinylsuafonyl groups in their side chains, 1,3,5-triacryloyl-hexabydro-s-triazine, bis(viaylaulfonyl)methane and the like); active halogen compounds (2,4-dichloro-6-hydroxy-s-triazine, sodium salt thereof and the like); mucohahlogenic acid (mucochloric acid, mucophenoxychloric acid and the like); isoxazoles; dialdehyde starc; 2-chloro-hydroxytrizinylated gelatin or the like can be used alone or two or more of them may be used in combination. Among then, active vinyl-type crosslinking agents are preferred. Amounts of the crosslinking agents to be used are not particularly limited. For example, the agents may be added in an amount of 0.1 to 20 mmol, more preferably 0.3 to 10 mmol based on 100 g of the hydrophilic binder.

Samples used for the method of the present invention are not particularly limited. For example, the method may be applied to samples whose content of a thiol group-containing compound need to be measured during chemical synthesis or chemical analysis, or biosamples isolated or collected from mammals including human and so forth. Examples of the biosample include, for example, blood, blood plasma, blood serum, tissues, tissue exudates and so forth. More specifically, applicable samples include blood-derived samples such as blood, blood plasma, and blood serum, cancer tissues isolated or collected from solid tumor tissues such as those of lung cancer, stomach cancer, esophagus cancer, breast cancer and brain tumor by surgical operation or histological tissue examination, destructive morbid tissues and exudates such as synovial membranes and osseous tissues of rheumatoid arthritis patients, and alveolodental membranes and osseous tissues of alveolus blennorrhoea patients, crevicular exudates of periodontal disease patients and so forth.

When the sample is a biotissue, for example, a slice having a thickness of about 1 to 10 µm, preferably 5 µm, can be prepared from a sample quickly frozen in liquid nitrogen by using a frozen slice preparation apparatus, and then put the slice on the thin membrane to have the sample contact with the thin membrane. When blood plasma or synovial fluid collected from a rheumatoid arthritis patient is used as a sample, about 1 to 30 µl, preferably 5 to 10 µl of the sample can be dropped onto the thin membrane. When crevicular exudate of a periodontal disease patient is used as a sample, an applicable method comprises the steps of inserting a filter paper strip into gingival crevice to collect about 5 to 10 µl of crevicular exudate, and then placing the filter paper on the thin membrane. After the collection of the crevicular exudate, the crevicular exudate may be optionally extracted from the filter paper by using distilled water or a suitable buffer (for example, 50 mM Tris-HCl, pH 7.6, 10 mM $CaCl_2$, 0.2 M NaCl and the like), and then the extract may be dropped onto the thin membrane.

The thin membrane of the present invention may preferably be formed on a flat surface of a support. Although material and form of the support are not particularly limited, the thin membrane way preferably be formed on a transparent or translucent support, for example, when the color change is observed under a microscope, or change on the surface is observed by spectroscopic means such as absorbance measurement or fluorescence measurement. Examples of such a transparent or translucent support include, for example, glass, transparent or translucent plastic films of polyethylene terephthalate, polycarbonate, polyimide, nylon, cellulose, cellulose triacetate and so forth. As glass, objective glass for microscopes is preferably used, and a polyethylene terephthalate film is preferably used as a plastic film.

Further, in addition to the transparent or translucent support mentioned above, an opaque support may also be used. For example, paper, synthetic paper, paper laminated with a synthetic resin such as polyethylene, polypropylene, polystyrene, and polyethylene naphthalate, metal plate such as plates made of aluminum, aluminum alloy, zinc, iron and copper, paper or plastic film laminated or evaporated with the metal mentioned above and so forth may be used. In the aforementioned embodiment, the support may be colored. However, the supports are not limited to those exemplified above so long as they allows formation of uniform thin membrane.

The thickness of the support is not also particularly limited. When glass is used, the thickness may preferably be approximately that of object glass (e.g., about 2 to 3 mm). When a polyethylene terephthalate film is used, the thickness may be about 100 to 250 $\mu$m, more preferably 160 to 200 $\mu$m, and most preferably about 175 $\mu$m. The thin membrane can be formed as a monolayer or multiple layers on the support as mentioned above, and the membrane should be formed so as to give a film having a thickness as constant as possible. For example, the membrane may preferably be formed to have a thickness of 0.2 to 10 $\mu$m, preferably about 0.5 to 6 $\mu$m, after dryness.

For preparation of the thin membrane, the microparticles of the substance selected from the group consisting of a metal and a metal compound, the hydrophilic binder, and optionally the crosslinking agent in respective given amounts may be added to water or an organic solvent such as methylene chloride, acetone, methanol, ethanol or a mixed solvent thereof and dispersed uniformly, and then the dispersion obtained may be applied onto a surface of a support and the resulting membrane may be dried. As application methods, for example, dip coating, roller coating, curtain coating, extrusion coating and so forth may be applied. However, the preparation methods of the thin membrane are not limited to these examples. For example, thin membrane-forming techniques commonly used in the field of photographic films and s0 forth can be also appropriately used.

The invention will be further explained wherein colloidal silver is used as the substance selected from the group consisting of a metal and a metal compound. In the field of silver halide color photographic photosensitive materials, colloidal silvers are generally used as yellow colloidal silver for a yellow filter and black colloidal silver for anti-halati n, and those c iloidal silvers can be used for the present invention. Orange brown or grayish brown colloidal silver may also be used in addition to the aforementioned examples. Among them, use of yellow colloidal silver having a maximum absorption wavelength of 400 nm to 500 nm is particularly preferred.

As methods for preparation of the colloidal silver, applicable methods include known methods, for example, a method utilizing reduction of a soluble silver salt with hydroquinone in a gelatin solution as disclosed in U.S. Pat. No. 2,688,601, a method utilizing reduction of a hardly soluble silver salt with hydrazine as disclosed in German Patent No. 1,096,193, a method utilizing reduction into silver with tannic acid as disclosed in U.S. Pat. No. 2,921,914, a method of forming silver grains by non-electrolysis galvanization as disclosed in Japanese Patent Unexamined Publication [Kokai] No. 5-134358/1993 and so forth. The method for preparing yellow colloidal silver by the doxtrin reduction technique of Carey Le disclosed in Weiser, "Colloidal Elements", Wiley & Sons, New York, 1933 may also be used.

When the thin membrane is formed on the support, an undercoat layer may be provided between the thin membrane and the support surface to improve adhesion of the thin membrane and the support. For example, a polymer or copolymer produced by polymerization of one or more kinds of monomers selected from vinyl chloride, vinylidene chloride, butadiene, methacrylic acid, acrylic acid, itaconic acid, maleic anhydride and so forth, or a polymer such as polyethyleneimine, epoxy resin, grafted gelatin, cellulose nitrate and so forth may be applied as the undercoat layer. When a polyester support is used, the adhesion between the support and the thin membrane may sometimes be improved by subjecting the support surface to corona discharge treatment, ultraviolet irradiation; or glow discharge treatment instead of providing an undercoat layer.

The term "thin membrane formed on a surface of a support" or synonyms thereof should not be construed to exclude those formed on one or more such undercoat layers and/or the treatment on a surface of a support. However, the means for improving adhesion between the thin membrane and the support are not limited to those mentioned above, and means commonly used in the field of photographic films and the like may also be appropriately applied. When the thin layer is composed of laminated two or more layers as mentioned above, an intermediate layer may be further provid d between the laminated layers. The term "laminated" used in the specification should not be construed to limit a membrane in which two layers are directly contacted. Means for appropriately providing intermediate layers are commonly used, for example, in the field of photographic films and so forth.

When the thin membrane is produced, other ingredients such as colorants, pigments, antiseptics, stabilizers and so forth may be incorporated in addition to the aforementioned ingredients. These ingredients are not particularly limited so long as they do not substantially affect the interaction between the thiol group-containing compound and the substance selected from the group consisting of a metal and a metal compound. Any materials may be appropriately chosen and used.

Modes for carrying out the method of the present invention are not particularly limited. For example, contact of the thin membrane and a sample may be achieved by, for example, dropping a liquid sample onto the thin membrane, or placing a tissue slice on the thin membrane. After optionally drying the liquid sample on the thin membrane, the thin membrane may be incubated preferably in a moist box, for example, at 37° C. for 6 hours or less, preferably 1 hour or less, and more preferably about 5 minutes to 90 minutes, or alternatively, at room temperature for 6 hours or less, preferably 1 hour or less, and more preferably about 5 minutes to 30 minutes.

When a thiol group-containing compound is contained in the sample, interaction arises between the compound and the microparticles of the substance selected from the group consisting of a metal and a metal compound in the thin membrane, and as a result, a color change such as coloring, decoloration, and color tone change occurs. The color change may be detected by suitable means, for example, visual observation or observation under a microscope, or spectroscopic measurement such as absorbance measurement and fluorescence measurement and so forth.

According to another embodiment of the method of the present invention, localization of a thiol group-containing compound derived from individual cells in a tissue can be accurately determined by preparing continuous frozen slices from a cancer tissue or the like, preparing an ordinary tissue preparation by hematoxylin-eosine staining or the like by using one of substantially contiguous two tissue slices, treating the other sample by the measurement method of the present invention, and then comparing or contrasting the both observation results. Further, when it is desired to determine localization of a thiol group-containing compound in one tissue slice, and desired to simultaneously observe cell nuclear morphology and so forth, a tissue sample may be treated by the measurement method of the present invention, and after color change occur as a result of the interaction between the microparticles of the substance selected from the group consisting of a metal and a metal compound in the thin membrane and the thiol group-containing compound, the membrane may preferably be subjected to nuclear staining by hematoxylin or the like. By applying the aforementioned method, localization of a thiol group-containing compound derived from individual cells can be more accurately determined.

EXAMPLES

The present invention will be explained more specifically with reference to the following examples. However, the scope of the present invention is not limited to these examples.

Example 1

Preparation of Thin Membrane for Measurement of Thiol Group-containing Compound (a) Monolayer Thin Membrane: Preparation of Sample 101

Acid-treated swine cutis gelatin (15 g) was dissolved in pure water (122 g), and the solution was added with colloidal silver and then with 1,2-bis(vinylsulfonylacetamido)ethane (4%, 0.6 ml) as a crosslinking agent The resulting solution was coated on object glass by using a wire bar coater so as to give a uniform membrane behaving a dry thickness of about 7 μm, and then dried to obtain a thin membrane. The thin membrane was stored at room temperature just before use. Yellow colloidal silver was prepared by adding an aqueous solution containing silver nitrate (17 g) to an aqueous solution (700 ml) containing dextrin (18 g), which was adjusted to pH 11.0, and then adding gelatin to the resulting mixture and washing the mixture with water by the known flocculation method. The mixture was further added with gelatin and warmed to 60° C. to give the desired colloidal silver. A coating aid was used for application, if needed.

(b) Monolayer Thin Membrane: Preparation of Membranes 102 to 125

Substances selected from the group consisting of a metal and a metal compound, hydrophilic colloids, hardening agents, and supports were changed or chosen as shown in Tables 1 and 2 to prepare Membranes 102 to 125 in the same manner as in th preparation of Membrane 101.

(c) Monolayer Thin Membrane: Preparation of Membranes 126 to 129

Membranes 126 to 129 were prepared in the same manner as in the preparation of Membrane 122 to 125 except that a slide coater was used instead of the wire bar coater for application. Drying was performed at ordinary temperature under ordinary humidity, after the membrane was cooled to 10° C. as required.

TABLE 1

| | Metal and/or metal compound | | | Hydrophilic binder | | Cross-linking agent | | |
| --- | --- | --- | --- | --- | --- | --- | --- | --- |
| Sample No. | Content[*1] | Mean particle size | Coated amount | Content[*2] | Film thickness | Content[*2] | Coated amount | Support Content[*4] |
| 101 | A | 0.01 μm | 0.04 g/m$^2$ | G | 7.0 μm | L | 0.60 g/m$^2$ | N |
| 102 | A | 0.01 μm | 0.37 g/m$^2$ | G | 7.0 μm | L | 0.60 g/m$^2$ | N |
| 103 | B | 0.05 μm | 0.37 g/m$^2$ | G | 7.0 μm | L | 0.60 g/m$^2$ | N |
| 104 | C | 0.05 μm | 0.37 g/m$^2$ | G | 7.0 μm | L | 0.60 g/m$^2$ | N |
| 105 | D | 0.05 μm | 0.37 g/m$^2$ | G | 7.0 μm | L | 0.60 g/m$^2$ | N |
| 106 | D | 0.09 μm | 0.37 g/m$^2$ | G | 7.0 μm | L | 0.60 g/m$^2$ | N |
| 107 | D | 0.50 μm | 0.37 g/m$^2$ | G | 7.0 μm | L | 0.60 g/m$^2$ | N |
| 108 | D | 1.00 μm | 0.37 g/m$^2$ | G | 7.0 μm | L | 0.60 g/m$^2$ | N |
| 109 | E | 1.00 μm | 0.37 g/m$^2$ | G | 7.0 μm | L | 0.60 g/m$^2$ | N |
| 110 | F | 0.01 μm | 0.37 g/m$^2$ | G | 7.0 μm | L | 0.60 g/m$^2$ | N |
| 111 | F | 0.01 μm | 0.37 g/m$^2$ | G | 3.0 μm | L | 0.60 g/m$^2$ | N |
| 112 | F | 0.03 μm | 0.37 g/m$^2$ | G | 1.0 μm | L | 0.60 g/m$^2$ | N |
| 113 | A | 0.01 μm | 0.37 g/m$^2$ | H | 7.0 μm | L | 0.60 g/m$^2$ | N |
| 114 | A | 0.01 μm | 0.37 g/m$^2$ | I | 7.0 μm | L | 0.60 g/m$^2$ | N |
| 115 | A | 0.01 μm | 0.37 g/m$^2$ | J | 7.0 μm | L | 0.60 g/m$^2$ | N |
| 116 | A | 0.01 μm | 0.37 g/m$^2$ | K | 7.0 μm | K | 0.60 g/m$^2$ | N |
| 117 | A | 0.01 μm | 0.37 g/m$^2$ | G | 7.0 μm | L | 2.40 g/m$^2$ | O |
| 118 | A | 0.01 μm | 0.18 g/m$^2$ | G | 7.0 μm | L | 2.40 g/m$^2$ | O |
| 119 | A | 0.01 μm | 0.18 g/m$^2$ | G | 5.0 μm | L | 1.70 g/m$^2$ | O |
| 120 | A | 0.01 μm | 0.18 g/m$^2$ | G | 3.0 μm | L | 1.00 g/m$^2$ | O |

TABLE 2

| | Metal and/or metal compound | | | Hydrophilic binder | | Cross-linking agent | | |
| --- | --- | --- | --- | --- | --- | --- | --- | --- |
| Sample No. | Content[*1] | Mean particle size | Coated amount | Content[*2] | Film thickness | Content[*2] | Coated amount | Support Content[*4] |
| 121 | A | 0.01 μm | 0.18 g/m$^2$ | G | 1.0 μm | L | 0.34 g/m$^2$ | O |
| 122 | A | 0.01 μm | 0.18 g/m$^2$ | G | 0.5 μm | L | 0.17 g/m$^2$ | O |
| 123 | A | 0.01 μm | 0.18 g/m$^2$ | G | 1.0 μm | L | 0.34 g/m$^2$ | P |

TABLE 2-continued

| | Metal and/or metal compound | | | Hydrophilic binder | | Cross-linking agent | | |
|---|---|---|---|---|---|---|---|---|
| Sample No. | Content[*1] | Mean particle size | Coated amount | Content[*2] | Film thickness | Content[*2] | Coated amount | Support Content[*4] |
| 124 | A | 0.01 μm | 0.18 g/m² | G | 1.0 μm | L | 0.34 g/m² | Q |
| 125 | A | 0.01 μm | 0.18 g/m² | G | 1.0 μm | L | 0.34 g/m² | R |
| 126 | A | 0.01 μm | 0.18 g/m² | G | 0.5 μm | L | 0.17 g/m² | O |
| 127 | A | 0.01 μm | 0.18 g/m² | G | 1.0 μm | L | 0.34 g/m² | P |
| 128 | A | 0.01 μm | 0.18 g/m² | G | 1.0 μm | L | 0.34 g/m² | Q |
| 129 | A | 0.01 μm | 0.18 g/m² | G | 1.0 μm | L | 0.34 g/m² | R |

Example 2

Measurement of a Thiol Group-containing Compound Using the Thin Membrane (a) Measurement for a Sample as a Solution As liquid samples for measurement of a thiol group-containing compound, solutions containing glutathione at a concentration of from 0.1 mmol/L to 1 mmol/L were used. Each liquid sample (about 10 μl) was dropped onto each of the thin membrane obtained in Example 1. The thin membranes were put into a moist box and incubated at 37° C. for 1 hour. Then, each thin membrane was evaluated by visual inspection. The results are shown in Table 3 (in the table, degree of color change is represented by the following symbols: *: slightly changed, : weakly changed, *: changed, **: clearly changed, and ***: very strongly changed). Visible color change was observed in each of the samples. In particular, the thin membranes containing colloidal silver gave strong red coloring.

TABLE 3

| Sample No. | Color change |
|---|---|
| 101 | * |
| 102 | **** |
| 103 | ** |
| 104 | ** |
| 105 | ** |
| 106 | ** |
| 107 | * |
| 108 | * |
| 109 | * |
| 110 | ** |
| 111 | *** |
| 112 | **** |
| 113 | **** |
| 114 | **** |
| 115 | **** |
| 116 | *** |
| 117 | *** |
| 118 | *** |
| 119 | *** |
| 120 | *** |
| 121 | **** |
| 122 | ***** |
| 123 | **** |
| 124 | **** |
| 125 | **** |
| 126 | ***** |
| 127 | **** |
| 128 | **** |
| 129 | |

(b) Measurement for a Frozen Slice Sample of a Biotissue

As biosamples, liver and spleen extracted from ICR mice were put on surfaces of thin membranes of No. 120 to 122 as frozen slices having a thickness of about 5 μm. The thin membranes were put into a moist box and incubated at 37° C. for 30 minutes. Evaluation of the activity was performed for each sample by (1) evaluation by visual inspection and (2) evaluation of microportions under a optical microscope. As a result, clearly stronger color development was observed for the membranes placed with the liver tissue slices than those placed with the spleen tissue slices. When the amounts of glutathione contained in the liver and spleen samples were separately quantified by high performance liquid chromatography, the amounts were found to be 9 mmol/kg for the liver and 1 mmol/kg for the spleen, which indicate a higher content in the liver and good correlation with the measurement by the thin membranes of the present invention (c) Measurement for a Cancer Tissue As test tissue samples, continuous slices each having a thickness of 5 μm were prepared from a frozen surgical; specimen of breast cancer. One of the slices was placed on object glass and dried, and then subjected to hematoxylin-eosine staining in a conventional manner. The other slices were placed on the gelatin thin membranes of Nos. 120 to 122 prepared in Example 1, and incubated in a moist box at 37° C. for 30 minutes. After the incubation, the thin membranes with the slice gave color changes, whilst the color of the other portions remained unchanged. Strong color change was observed particularly in cells at peripheries of cancer lesions for all of the cancer tissues. The thin membranes of the present invention gave color change precisely in the same area as portions diagnosed as cancer cells by the hematoxylin-eosine staining.

Example 3

Measurement of a Compound not Containing Thiol Group by Using the Thin Membrane (Comparative Example)

As liquid samples of compounds not containing thiol group, solutions of glycine, histidine, methionine, cystine, methyl ethyl keton, and chloral hydrate in water r ethanol at a concentration of from 0.1.mmol/L to 1 mm l/L were used. Each sample in an amount of about 10 μl was dropped onto each of the thin membranes of Nos. 117 to 122 obtained in Example 1. The thin membranes were incubated in a moist box at 37° C. for 30 minutes, and then evaluation by visual inspection was carri d out for each of the samples, As a result, no sample gave significant color change.

Industrial Applicability

According to the method of the present invention, a thiol group-containing compound present in a solution or a biotissue can be determined accurately and conveniently, and results of evaluation can be obtained in a short period of time. Moreover, according to the method of the present invention, a thiol group-containing compound can be measured in an extremely small amount of sample. A thiol group-containing compound localized in individual cells in a tissue can be measured, and a thin membrane after the measurement can be stored as a preparation for a long period of time.

What is claimed is:

1. A thin membrane used for measurement of a thiol group-containing compound, which comprises a microparticle of a metal and comprises a hydrophilic binder wherein the thin membrane is dry.

2. The thin membrane according to claim 1 which further comprises a crosslinking agent.

3. The thin membrane according to claim 1 or claim 2, which generates a color change by interaction of the thiol group-containing compound and the microparticle.

4. The thin membrane according to claim 1, wherein said microparticle has a particle size of 0.001 $\mu$m to 1 $\mu$m.

* * * * *